(12) United States Patent
Ostermaier et al.

(10) Patent No.: US 7,517,985 B2
(45) Date of Patent: Apr. 14, 2009

(54) PROCESS FOR MAKING SOLID TRIPHENYLBORON-PYRIDINE OR ITS ADDUCT

(75) Inventors: John J. Ostermaier, Orange, TX (US); Michael L. Bourgeois, Orange, TX (US)

(73) Assignee: Invista North America S.A R.L., Wilmington, DE (US)

( * ) Notice: Subject to any disclaimer, the term of this patent is extended or adjusted under 35 U.S.C. 154(b) by 341 days.

(21) Appl. No.: 11/473,907

(22) Filed: Jun. 23, 2006

(65) Prior Publication Data

US 2007/0299259 A1    Dec. 27, 2007

(51) Int. Cl.
*C07F 5/02*    (2006.01)
(52) U.S. Cl. ........................................... 546/13
(58) Field of Classification Search ..................... 546/13
See application file for complete search history.

(56) References Cited

U.S. PATENT DOCUMENTS 3,211,679 A    10/1965    Updegraff

FOREIGN PATENT DOCUMENTS

| JP | 08-311074 | 11/1996 |
| JP | 2003238572 | * 8/2003 |

* cited by examiner

*Primary Examiner*—Charanjit S Aulakh

(57) ABSTRACT

A process for producing solid triphenylboron-pyridine (TPBP) spherical particles by separately feeding into a vigorously agitated reaction zone (i) a stream of pyridine and a (ii) stream comprising a solution of sodium hydroxide adduct of triphenylboron (TPBA) whereby the total concentration of TPBA in the combined feed streams is in the range of from 1 wt % to 6 wt %, and simultaneously removing a product stream from said reaction zone and recovering the triphenylboron-pyridine (TPBP) particles.

4 Claims, 2 Drawing Sheets

PROCESS FOR MAKING SOLID TRIPHENYLBORON-PYRIDINE OR ITS ADDUCT

FIELD OF THE INVENTION

The present invention relates to a process of producing triphenylboron-amine compounds, and, more particularly, to a process for producing solid triphenylboron-pyridine by a controlled precipitation reaction between pyridine and triphenylboron-sodium hydroxide adduct.

BACKGROUND

Triphenylboron-amine compounds and triphenylboron-pyridine (TPBP), in particular, are known to be effective biocides and marine anti-fouling agents and are, therefore, commercially important compounds. U.S. Pat. No. 3,211,679, for example, describes antifouling compositions comprising triphenylboraneamine complexes which provide good protection from marine fouling.

One method for producing TPBP is by the reaction of aqueous triphenylboron-NaOH adduct (NaΦ$_3$BOH or TPBA) or triphenylboron-KOH adduct with pyridine in aqueous solution as shown in JP Publication No. 08-311074 (Yoshitomi Pharm Ind KK). Solid TPBP particles precipitate out with the progress of the reaction which can be from 30 minutes up to two days.

However, the particles formed by the above process are often of irregular shape and of undesirable particle size distribution to the extent that recovery of the solid particles using solid-liquid separation and drying methods can be difficult. It would thus be desirable to have a process that would produce solid TPBP particles of generally round, i.e., spherical, shape having a mean diameter greater than about 20 microns and a Gaussian particle size distribution that can be more efficiently recovered using available solid-liquid separation and drying methods. The present invention provides such a process that can be implemented on a commercial scale.

SUMMARY OF THE INVENTION

The present invention is an improved process for producing triphenylboron-pyridine (TPBP) comprising generally spherical solid particles which comprises:

(1) forming a suspension of solid TPBP particles in aqueous mother liquor in a reaction zone equipped with means for agitating the suspension, (2) separately feeding into said reaction zone (i) a stream of pyridine and a (ii) stream comprising a solution of sodium hydroxide adduct of triphenylboron (TPBA) whereby the total concentration of TPBA in the combined feed streams is in the range of from 1 wt % to 6 wt %, and (3) simultaneously removing a product stream from said reaction zone at a rate whereby the original volume of said suspension in the reaction zone remains substantially constant, and the concentration of solid TPBP in the suspension is maintained at a value of less than 8 wt %.

In a preferred embodiment of the invention, the total concentration of TPBA in the combined feed streams is in the range of from 3.7 wt % to 5 wt %, and the temperature of the suspension in the reaction zone is in the range of from about 20° C. to about 60° C., with 35° C. to 45° C. being the preferred temperature range for continuous operation.

DETAILED DESCRIPTION OF THE INVENTION

Figure 1:
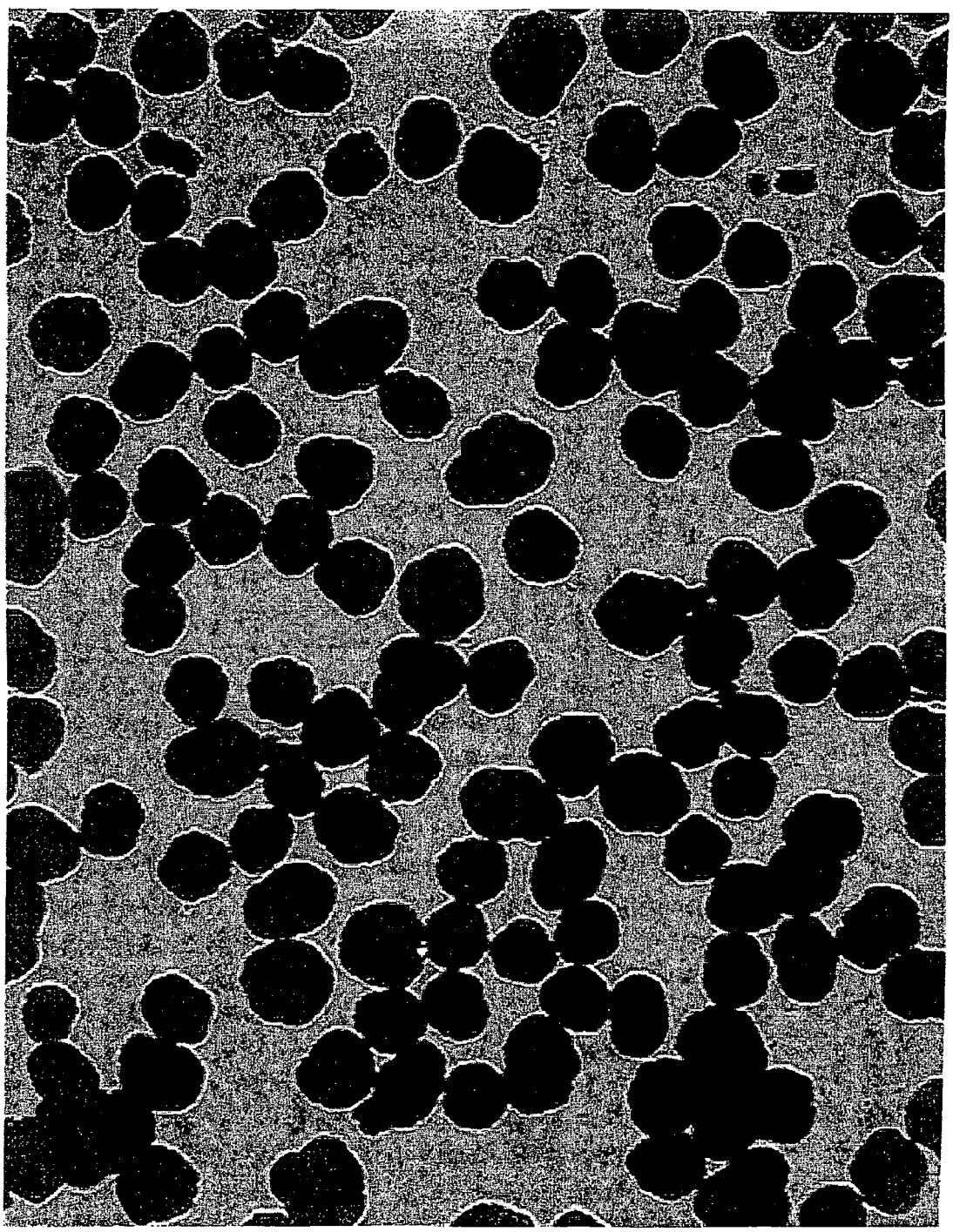
FIG. 1 is a photomicrograph of generally spherical TPBP particles that were produced according to the invention and as described in Example 5.

To practice the process of this invention, a pyridine-containing stream and a stream of solution of sodium hydroxide adduct of triphenylboron ("TPBA solution") are fed, as by metering, separately into a reaction zone, i.e., a reactor, crystallizer, or other suitable vessel, that contains a previously formed suspension of solid TPBP particles in an aqueous mother liquor. The term "mother liquor" is used herein to describe the liquid phase in the reactor or crystallizer, which includes sodium chloride and caustic (NaOH) dissolved in water.

The reaction zone is equipped with an agitator for vigorously agitating the suspension during operation of the process. The term "vigorous agitation" as used herein is well within the skill in the art and is intended to mean well agitated and continuous mixing of the suspension in the reactor that is designed to insure uniform and generally rapid mixing of the reactant streams as they are introduced into the reactor. During continuous operation of the process, a product stream is simultaneously withdrawn from the suspension, and the feed rates, or flow rates, of the pyridine-containing stream, the TPBA solution stream and the product stream are adjusted so that the volume of suspension in the reaction zone is maintained at a predetermined generally constant value. There is nothing critical with respect to the predetermined volume of the suspension maintained in the reaction zone. Maintaining a convenient volume of suspension in the reaction zone in correspondence with the size of the reactor and the agitator capability will produce satisfactory results.

The TPBA solution reacts with pyridine to form solid TPBP particles, i.e., one mole of pyridine and one mole of TPBA react to form one mole of TPBP and one mole of NaOH.

It has now been discovered according to the invention that generally spherical shaped TPBP particles having a mean diameter greater than about 20 microns and a Gaussian particle size distribution can be consistently produced on a continuous basis. The TPBP particles are recovered as a filter cake, and the filter cake in the recovery process exhibits improved properties with respect to filtration, washing, and drying when the TPBA content of the combined TPBA solution stream and pyridine stream is maintained in a specified range from about 1 wt % to about 6 wt %. Although for best results in terms of ease of operation, the TPBA concentration of the combined TPBA solution stream and pyridine stream should preferably be in the range of from 3.7 wt % to about 5 wt %.

Introduction of the pyridine-containing stream and the TPBA solution stream and removal of the product stream should preferably be conducted on a continuous basis for best results, however, the process can also be run on an intermittent basis. The pyridine-containing stream can be undiluted pyridine or diluted with an aqueous mother liquor or water. Solid TPBP can be recovered from the product stream by filtration or by any other convenient solid-liquid separation technique. Typical devices include rotary vacuum filters and centrifuges.

Temperature can have an effect on the characteristics of the TPBP particles formed. Higher temperatures generally favor larger particles, although temperatures above 60° C. have been observed to cause undesirable changes in product morphology. For best results in carrying out the process the temperature in the reaction zone, i.e., the temperature of the suspension in the reaction zone, should be in the range of from about 20° C. to about 60° C. The preferred operating temperature is in the range of 35° C. to 45° C.

The concentration of NaOH in TPBA solution can vary over a wide range, but best results have been observed when the NaOH concentration is in the range of from about 1.9 wt % to 2.3 wt % of the solution (based on the TPBA solution only). The TPBA solution may contain other components, such as sodium chloride, at a concentration in the range of from about 4.1 wt % to 5.0 wt % of the solution (based on the TPBA solution only).

To begin the process, a suspension of solid TPBP particles is formed in the reaction vessel by an initial batch-wise precipitation reaction between pyridine and TPBA solution. A suspension held over from a previous operation of the process is preferred.

A reactor for carrying out the process can be a crystallizer with a suitable agitation or other mixing device. The size of the reaction vessel is chosen to give a residence time (defined as the volume of the vessel divided by the total volumetric feed rate) greater than about 10 minutes. Agitation can be provided by an agitator or by a circulation loop or by both means. Reactor vessels, such as crystallizers, will typically be equipped with a draft tube and/or internal baffles arranged about the periphery of the vessel.

EXAMPLES

All experiments were performed in a 1-Liter cylindrical vessel, which had a height to diameter ratio of contained fluid of 1.0. The vessel had four baffles with standoffs, and was equipped with a six-blade turbine agitator. The agitator was a Rushton turbine having 6 generally flat blades with the turbine section being 2 inches in diameter and tuning at 300 rpm. There were two feed points located at the same elevation as the turbine blades, and product was withdrawn by overflow from an upper part of the vessel.

In batch runs, the TPBA solution was added to the vessel, then pyridine was added continuously over a period of time. In continuous runs, sufficient water was added to the vessel to just submerge the agitator blades, then both reactants were simultaneously fed to the vessel. In all cases, one mole of pyridine was added to one mole of TPBA.

The product stream comprised a slurry, i.e., a suspension, of TPBP particles that was characterized in the following ways in order to evaluate the quality of the product:

Photomicrographs were taken to observe particle size and shape,

Particle size analysis to determine particle size,

Cake moisture to determine the amount of water in the cake recovered after filtration, and Filter cake resistance to determine the ease of filtration.

Filter cake resistance was determined by filtering three different volumes of slurry (50, 75, and 100 mL) through a Buchner filter funnel, and measuring the volume of filtrate (V) recovered and filtration time (t) for each measurement. Then t/V was plotted versus V for each measurement. The slope of this plot is related to the filter cake resistance by the expression $$\alpha(m/kg) = 2\, A^2 (\Delta P)(\text{slope})/\mu w$$

where:
$A$=filter area ($m^2$)
$\Delta P$=pressure drop across cake and filter medium (Pa)
$\mu$=liquid viscosity (Pa sec)
$w$=ratio of cake solids to filtrate volume ($kg/m^3$)

Cake moisture was determined by weighing the wet filter cake to get the weight of water plus solids, followed by drying in a vacuum oven and reweighing to obtain the weight of dry solids. Cake moisture was calculated as follows:

Cake Moisture=(Wt of wet cake−Wt of dry solids)/Wt of dry solids

Example 1

Rapid Batch Precipitation using a 7.5 wt % TPBA Solution

In this experiment a 7.5 wt % TPBA solution was placed in reaction vessel, and undiluted pyridine was rapidly poured into the stirred vessel at room temperature. The contents were allowed to digest for 30 minutes forming a slurry, and then the slurry was characterized. The slurry that was produced had the consistency of whipped cream, and showed no settling. Mean particle size was 7 microns, and the particles were fine needles. Filtration was extremely slow, with a filter cake resistance of $2.3 \times 10^{11}$ m/kg.

Example 2

Slow Batch Precipitation using a 7.5 wt % TPBA Solution

This example was identical to Example 1, with the exception that undiluted pyridine was added slowly over a period of 1 hour. The slurry had the consistency of milk. The mean particle size was 29 microns, and the particles were needle shaped. The filtration rate was slow with a filter cake resistance of $2.5 \times 10^{10}$ m/kg. Cake moisture was 2.55 grams of water per gram of dry solid.

Example 3

Slow Batch Precipitation using a 3.7 wt % TPBA Solution

This example was the same as Example 2, except that a 3.7 wt % TPBA solution was used. The mean particle size was 15 microns, and the particles were needle shaped. The filtration rate was slow with a filter cake resistance of $1.8 \times 10^{10}$ m/kg. Cake moisture was 2.58 grams of water per gram of dry solid.

Example 4

Slow Batch Precipitation at 40° C. using a 7.5 wt % TPBA Solution

This example was the same as Example 3, except the temperature of the suspension in the reaction vessel was maintained in the range of 40° C. instead of room temperature. The mean particle size of the resulting TPBP was 30 microns, and the crystals were less needlelike and more granular. The filtration rate increased noticeably, with a filter cake resistance of 6.2×10$^9$ m/kg. Cake moisture was 2.74 grams water per gram of dry solid.

Example 5

Continuous Precipitation at 40° C. using a 3.7 wt % TPBA Solution

In this example a 3.7 wt % TPBA solution and an undiluted pyridine stream were used as feed streams. The TPBA solution was fed continuously to the reaction vessel, simultaneously with a stoichiometric amount of pyridine. The reactant streams were fed on opposite sides of the agitator blades. The temperature of the suspension in the reaction vessel was controlled at 40° C. A product stream was removed continuously from the reaction vessel. The residence time in the reaction vessel was 1 hour (based on the flow rate of product stream removal). TPBP particles that were obtained were generally round or micro-spheres in shape, rather than the needles and granules obtained from batch precipitation in previous examples. FIG. 1 is a photomicrograph of the TPBP particles recovered according to this example. The mean particle size of the particles was 64 microns. The filter cake resistance was 3.9×10$^8$ m/kg, i.e., over an order of magnitude lower than filter cake resistance observed in the best batch run. Cake moisture was 0.18 grams of water per gram of dry solid, which is about one-twelfth of the moisture concentration as compared to the batch runs.

Example 6

Continuous Precipitation at 40° C. using a 7.5 wt % TPBA Solution

This example was identical to Example 5, except a 7.5 wt % TPBA solution was used instead of a 3.7 wt % TPBA solution. The particles obtained in this example were fine needles, very similar to those obtained in previous batch experiments, the mean particle size being 6 microns. The recovered material filtered very slowly, and the filter cake resistance was 5.2×10$^{10}$ m/kg, over 100 times higher than that in Example 5. Cake moisture was 1.25 grams of water per gram of dry solid, which is much higher than that in Example 5.

Example 7

Continuous Precipitation at 45° C. using a 7.5 wt % TPBA Solution

Figure 2:
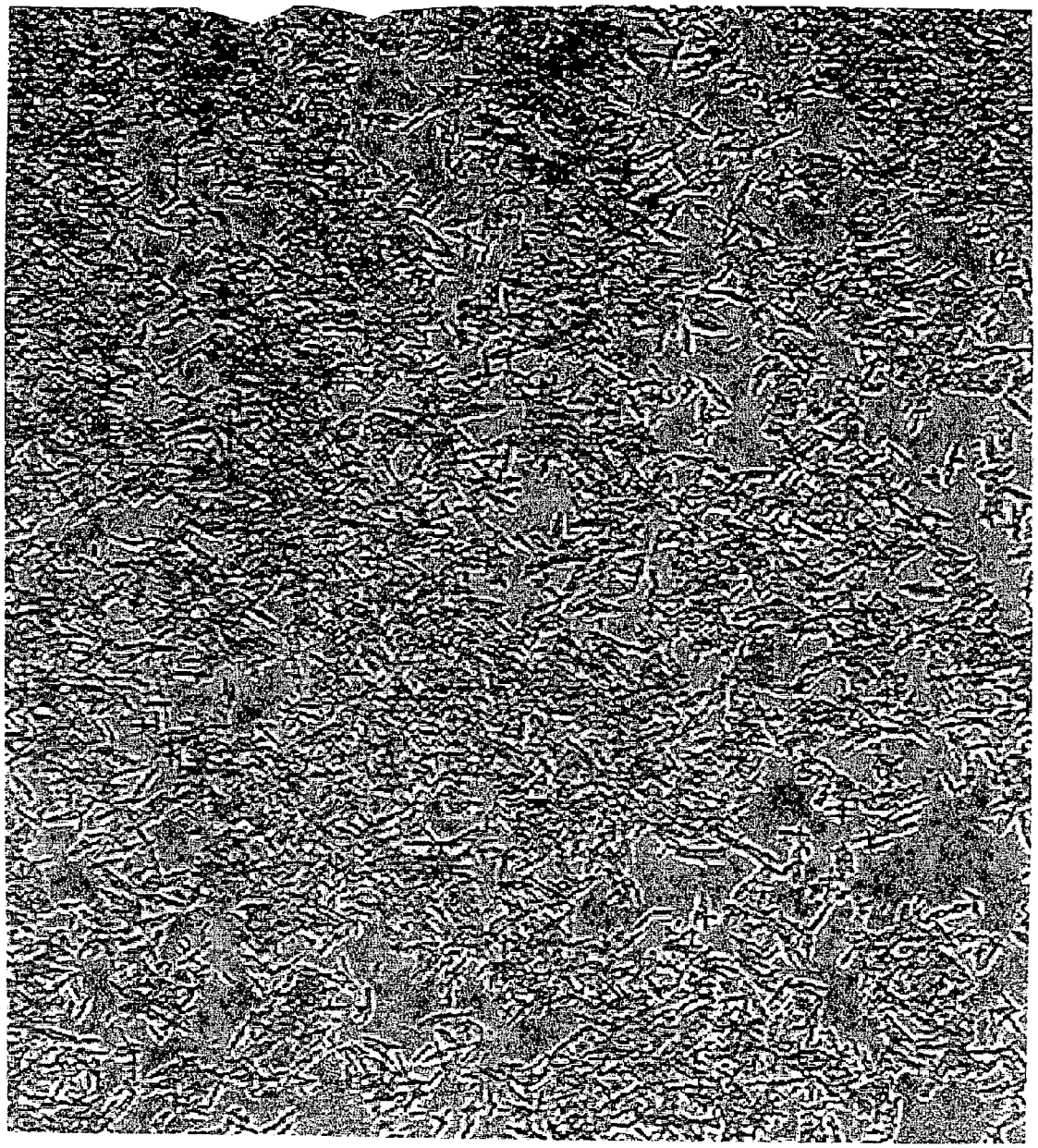
FIG. 2 is a photomicrograph of generally needle-like, irregularly-shaped, TPBP particles produced as described in Example 7.

The experimental conditions for this example were identical to those of Example 6, except that the temperature of the suspension was controlled at 45° C. TPBP particles obtained in this example were fine needles, very similar to those obtained in the previous batch experiments. FIG. 2 is a photomicrograph of the particles recovered in this example. The mean particle size was 18 microns with a median of 5.5 microns (bimodal particle size distribution).

Example 8

Continuous Precipitation at 40° C. using a 5.9 wt % TPBA Solution

This example was identical to Example 5, except that a 5.9 wt % TPBA solution was used instead of 3.7 wt % TPBA solution. The particles obtained in this example were a mixture of generally round particles, or micro-spheres, and small granules. The mean particle size was 77 microns. The slurry filtered rapidly, and the filter cake resistance was 7.5×10$^8$ m/kg. The cake moisture was 0.14 grams of water per gram of dry solid.

Example 9

Continuous Precipitation at 40° C. using a 5.0 wt % TPBA Solution

This example was identical to Example 5, except that a 5.0 wt % TPBA solution was used instead of 3.7 wt % TPBA solution. The particles obtained in this experiment were generally round or micro-spheres. The mean particle size was 35 microns. The slurry filtered rapidly, and the filter cake resistance was 5.6×10$^8$ m/kg. The cake moisture was 0.22 grams of water per gram of dry solid.

The invention claimed is:

1. A process for producing triphenylboron-pyridine (TPBP) comprising generally spherical solid particles which comprises:
    (1) forming a suspension of solid TPBP particles in aqueous mother liquor in a vigorously agitated reaction zone,
    (2) separately feeding into said vigorously agitated reaction zone (i) a stream of pyridine and a (ii) stream comprising a solution of sodium hydroxide adduct of triphenylboron (TPBA) whereby the total concentration of TPBA in the combined feed streams is in the range of from 1 wt % to 6 wt %, and
    (3) simultaneously removing a product stream from said reaction zone at a rate whereby the original volume of said suspension in the reaction zone remains substantially constant, and the concentration of solid TPBP in the suspension is maintained at a value of less than 8 wt %.

2. The process of claim 1 the total concentration of TPBA in the combined feed streams is in the range of from 3.7 wt % to 5 wt %.

3. The process of claim 1 or claim 2 in which the temperature of the suspension of solid TPBP particles in aqueous mother liquor in the reaction zone is maintained in the range of from about 20° C. to about 60° C.

4. The process of claim 3 in which the temperature is maintained in the range of from 35° C. to 45° C.

* * * * *